United States Patent

Chang et al.

[11] Patent Number: 5,901,708
[45] Date of Patent: May 11, 1999

[54] METHOD AND APPARATUS FOR FORMING ULTRASONIC THREE-DIMENSIONAL IMAGES USING CROSS ARRAY

[76] Inventors: Seong-Ho Chang, 306-1504, Daochung Apt. Kaspo-dong., Kangnam-gu, Seoul; Tai-Kyung Song, A-6 Kwahakwan Apt., #109-112, Hoegi-dong., Tongdasmun-gu, Seoul, both of Rep. of Korea

[21] Appl. No.: 08/942,348

[22] Filed: Oct. 1, 1997

[30] Foreign Application Priority Data

Oct. 1, 1996 [KR] Rep. of Korea ................. 1996-43565

[51] Int. Cl.⁶ ....................................................... A61B 8/00
[52] U.S. Cl. .......................................... 128/916; 600/443
[58] Field of Search ................................... 128/660, 916; 600/443, 437

[56] References Cited

U.S. PATENT DOCUMENTS

| | | | |
|---|---|---|---|
| 4,694,434 | 9/1987 | Ramm et al. | 128/660 |
| 5,379,769 | 1/1995 | Ito et al. | 600/443 |
| 5,704,361 | 1/1998 | Seward et al. | 128/916 |
| 5,797,845 | 8/1998 | Barabash et al. | 128/916 |

Primary Examiner—Francis J. Jaworski
Assistant Examiner—Ali M. Imam
Attorney, Agent, or Firm—Dilworth & Barrese

[57] ABSTRACT

An ultrasonic three-dimensional image formation apparatus forms ultrasonic three-dimensional images from ultrasonic echoes using a cross array including two linear phased arrays. Thus, an ultrasonic three-dimensional image can be obtained using a small amount of data to thereby enable a real-time three-dimensional image formation.

22 Claims, 3 Drawing Sheets

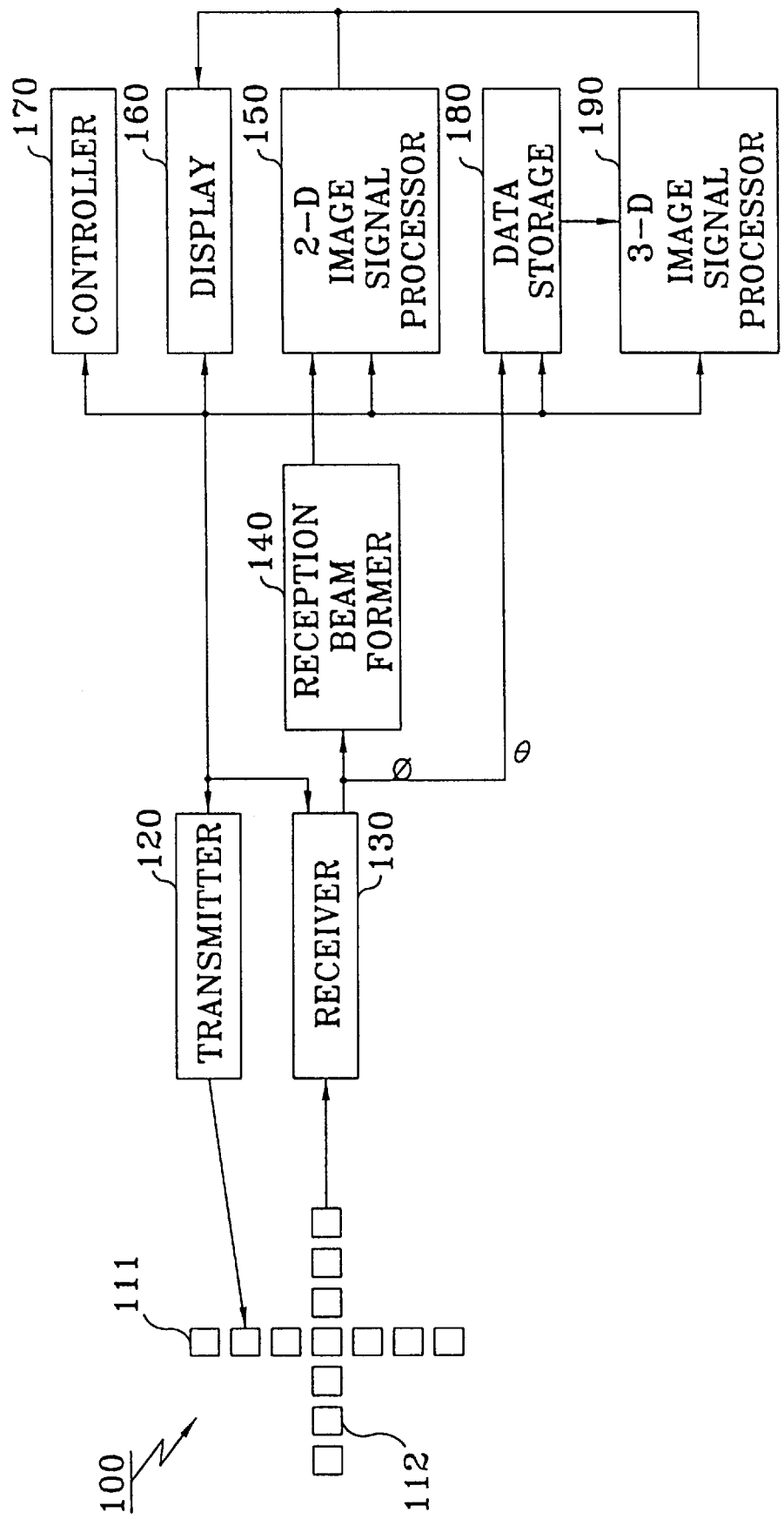

METHOD AND APPARATUS FOR FORMING ULTRASONIC THREE-DIMENSIONAL IMAGES USING CROSS ARRAY

BACKGROUND OF THE INVENTION

The present invention relates to a method for forming ultrasonic three-dimensional images and an apparatus therefor, and more particularly, to a method for forming ultrasonic three-dimensional images on a real time basis using a cross array including two linear phased arrays and an apparatus therefor.

Recent medical ultrasonic scanners for obtaining ultrasonic images uses linear or convex phased arrays containing 256 transducer elements, in order to electronically steer and focus a ultrasonic beam in an image formation plane. The transducer elements forming the array transducers are arranged linearly to only one direction, for example, to an azimuth direction. As a result, such linear phased arrays can be focused in only the azimuth direction, so that only a single plane of an image is provided at a fixed elevation direction (usually 0 degree).

A mechanical scan is performed using a motor in an elevation direction and an electric scan is performed in the azimuth direction, in order to obtain a three-dimensional image using such linear phased arrays. As a result, the image planes constituting a three-dimensional image are obtained from elevational directions differing from each other as necessary in a desired three-dimensional scan area. However, since the beam width in an elevation direction, that is, the thickness of an image plane is fixed by a mechanical lens, a scan time is very long for obtaining a three-dimensional image with respect to a desired area.

When compared with the linear phased arrays, the two-dimensional arrays in which array transducers are arranged in two directions, can perform an electric scan with respect to any direction, thereby enabling dynamic focusing in both an azimuth direction and an elevation direction. Accordingly, the two-dimensional array can provide a more improved image than the linear phased arrays, and enables a more efficient three-dimensional image formation.

However, since the two-dimensional array is generally comprised of the number of transducer elements much more than that of linear phased arrays (typically from 1000 to 4096), the ultrasonic three-dimensional image formation apparatus using the two-dimensional array is unrealistically high in complexity, size and cost. Also, an image scan time consumed for scanning a desired three-dimensional scan area using a two-dimensional array is much longer than a two-dimensional scan time using a linear phased array. For example, when sectional images corresponding to 64 different elevation directions in a desired three-dimensional scan area are required, the two-dimensional array requires an image scan time 64 times that of the linear phased array. Thus, the three-dimensional image formation using the two-dimensional array is limited in its application.

SUMMARY OF THE INVENTION

Thus, it is an object of the present invention to provide a method for forming an ultrasonic three-dimensional image on a real time basis, at the same speed as that taken when obtaining an existing two-dimensional image, using a cross array including two linear phased arrays.

It is another object of the present invention to provide an apparatus for forming an ultrasonic three-dimensional image on a real time basis, using a cross array including two linear phased arrays.

To accomplish the above object of the present invention, there is provided a method for forming an ultrasonic three-dimensional image using ultrasonic echoes, the method comprising the steps of:

(a) forming a cross array by aligning a first linear phased array and a second linear phased array to cross perpendicular to each other and sharing a center transducer element, each of the first and the second linear phased arrays having linearly aligned, a predetermined size of square transducer elements, respective square transducer elements having a predetermined inter-element spacing;

(b) transmitting ultrasonic waves via the first linear phased array so that all transmission beam planes necessary for scanning a desired three-dimensional area are formed;

(c) receiving, via the second linear phased array, ultrasonic echoes produced by which the ultrasonic waves transmitted in step (b) are reflected from the desired three-dimensional area;

(d) performing a parallel beam forming with respect to the ultrasonic echoes received in step (c), in order to obtain an ultrasonic signal involving a three-dimensional image from scan lines formed by individually crossing all the received beam planes necessary for scanning the desired three-dimensional area with each transmission beam plane formed in step (a); and (e) obtaining three-dimensional image information by signal-processing the ultrasonic signal obtained in step (d).

To accomplish the other object of the present invention, there is also provided an apparatus for forming an ultrasonic three-dimensional image using ultrasonic echoes, the apparatus comprising:

a cross array which is formed by aligning a first linear phased array and a second linear phased array to cross perpendicular to each other and sharing a center transducer element, each of the first and the second linear phased arrays having, linearly aligned, a predetermined size of square transducer elements, respective square transducer elements having a predetermined inter-element spacing; a transmitter for transmitting ultrasonic waves via the first linear phased array so that transmission beam planes necessary for scanning a desired three-dimensional area are formed along elevation directions; a receiver for receiving ultrasonic echoes via the second linear phased array in which the ultrasonic echoes are obtained from each transmission beam pane formed by the transmitter, and converting the received ultrasonic echoes into digital form to then output the converted result; a beam former for storing the digital ultrasonic signals output from the receiver, and performing a parallel beam forming with respect to the stored ultrasonic signals in order to generate an ultrasonic signal involving a three-dimensional image from scan lines which are formed by individually crossing of all the received beam planes necessary for scanning a desired three-dimensional area with the transmission beam planes; and an image signal processor for signal-processing the ultrasonic signal beam-formed in the beam former and generating three-dimensional image information.

BRIEF DESCRIPTION OF THE DRAWINGS

The preferred embodiments are described with reference to the drawings wherein:

FIG. 3 is a block diagram showing an ultrasonic three-dimensional image formation apparatus according to another preferred embodiment of the present invention, in which the three-dimensional image formation method according to the present invention is embodied using an existing two-dimensional image formation apparatus.

DETAILED DESCRIPTION OF THE PREFERRED EMBODIMENTS

Preferred embodiments of the present invention will be described in detail with reference to the accompanying drawings.

The present invention provides the structure of an ultrasonic array transducer including transducer elements of the remarkably small number in comparison with conventional two-dimensional arrays, and enabling a three-dimensional scan within a typical two-dimensional image scan time, and a new three-dimensional image formation method and apparatus using the same.

Figure 1:
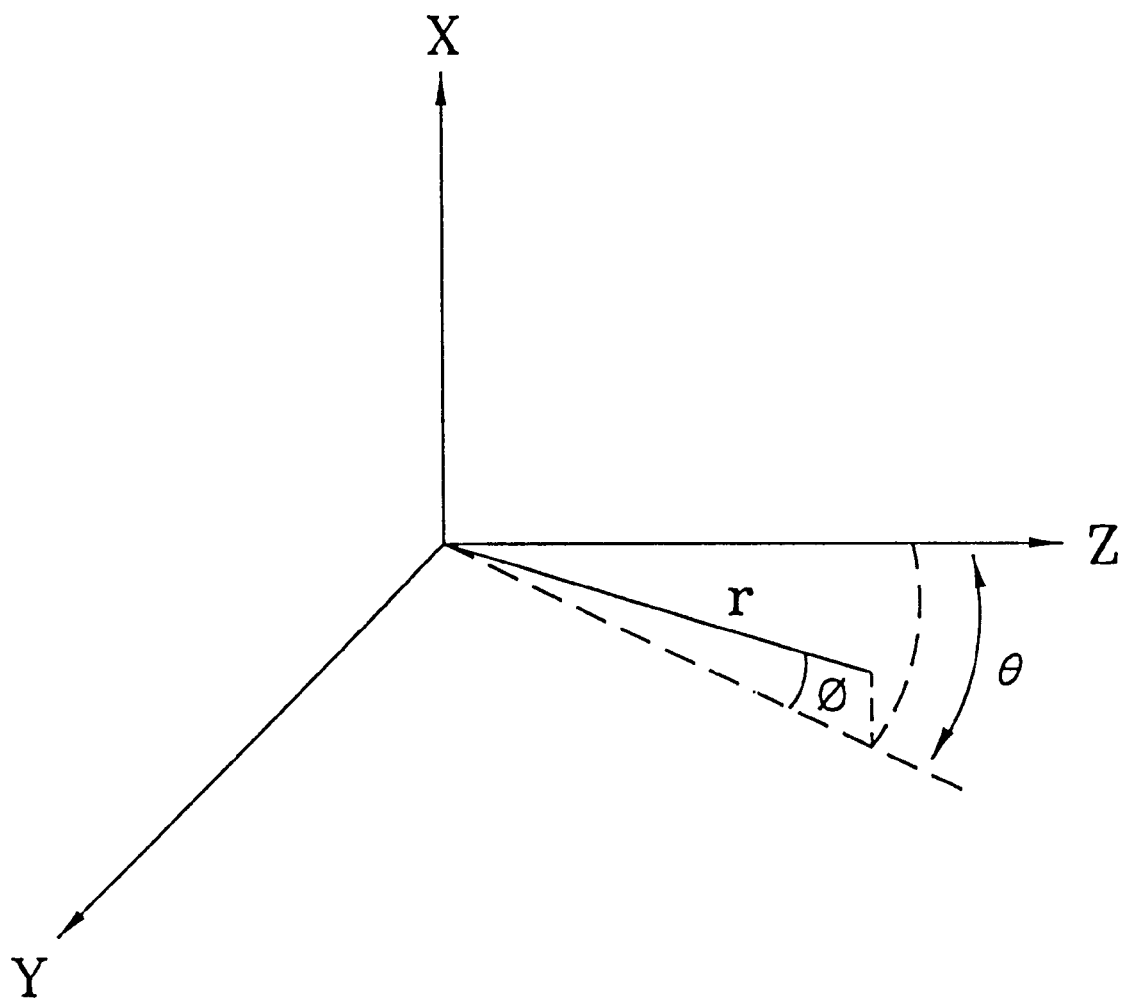
FIG. 1 is a view showing a coordinate system used for explaining a three-dimensional image formation method and apparatus according to the present invention.
Figure 2:
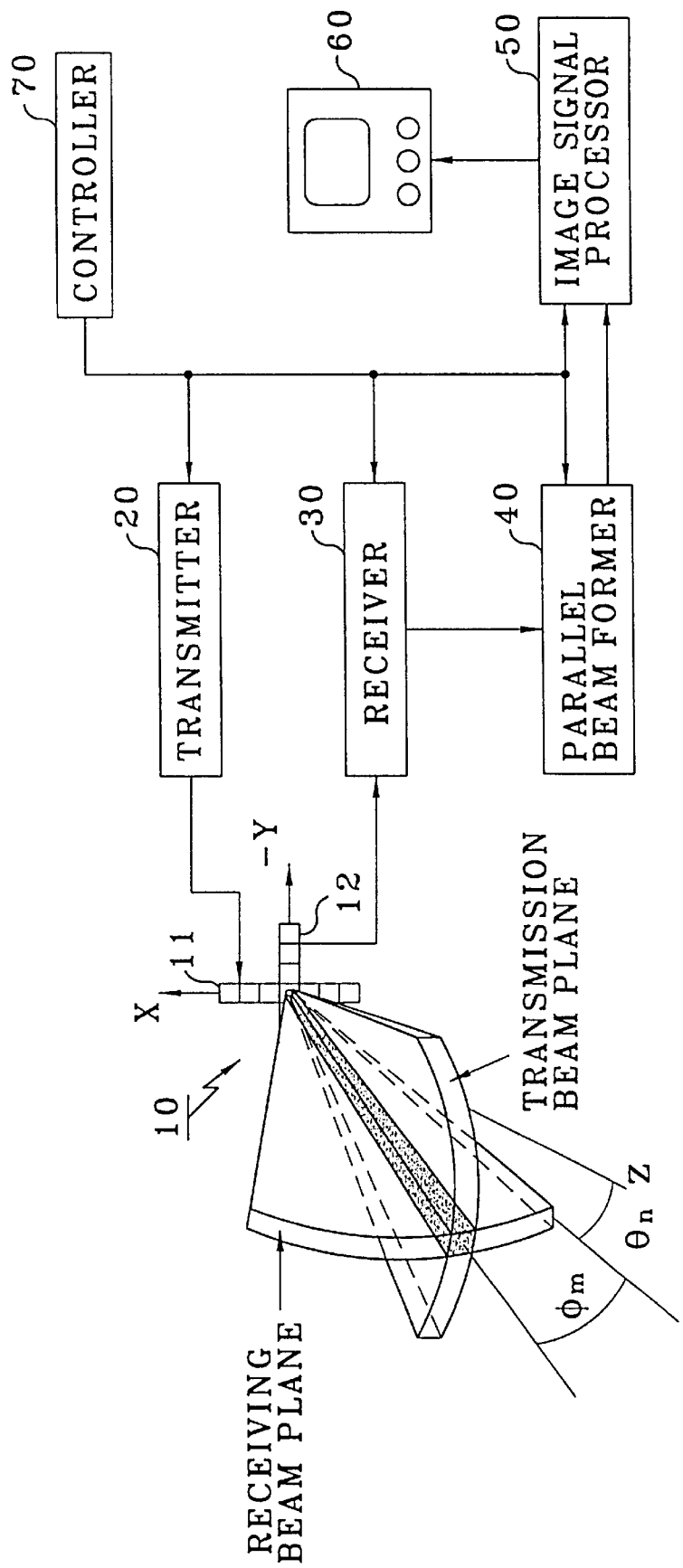
FIG. 2 is a block diagram showing an ultrasonic three-dimensional image formation apparatus using a cross array according to a preferred embodiment of the present invention.

Referring to FIG. 2, an ultrasonic three-dimensional image formation apparatus using a cross array according to a preferred embodiment of the present invention includes a cross array 10 constituted by two linear phased arrays 11 and 12 perpendicular to each other. Each of the transmission linear phased array 11 and the reception linear phased array 12 has an inter-element spacing of $\lambda/2$ in which $\lambda$ is the ultrasound wavelength and includes L square transducer elements the length whose one side is slightly smaller than $\lambda/2$. The two linear phased arrays 11 and 12 share one transducer element positioned in an origin on the X-Y coordinate axes as a respective center array element. The transmission linear phased array 11 is used for transmission of ultrasonic waves, and arranged in the X-axis direction in FIG. 2. The receiving linear phased array 12 is used for reception of ultrasonic echoes, and arranged in the Y-axis direction in FIG. 2. The number of transducer elements constituting each linear phased array 11 or 12 is preferably 64 or 128. The squares shown in the X-axis and the Y-axis of FIG. 2 are transducer elements constituting the transmission linear phased array 11 and the reception linear phased array 12.

A transmitter 20 supplies an electrical signal for generation of ultrasonic waves to the transmission linear phased array 11. The ultrasonic waves transmitted by the transmission linear phased array 11 in the focusing form on a focal point are reflected by obstacles while travelling in the human body. The ultrasonic echoes returning to a cross array 10 are converted into electrical signals by the transducer elements in the reception linear phased array 12. A receiver 30 receives the electrical signals output from the reception linear phased array 12 and converts the received analog electrical signal into digital form after performing various signal processing procedures which are performed in a typical ultrasonic image formation apparatus with respect to the received analog electrical signals. A parallel beam former 40 performs a parallel beam forming with respect to the digital signals supplied from the receiver 30. An image signal processor 50 receives all scan line signals generated in the parallel beam former 40 and performs various image and picture processing procedures with respect to the received signal in order to generate an image signal in various forms to be displayed on a display 60. A controller 70 controls the operations of the above-described blocks to obtain a three-dimensional image in desired form.

When the transmitter 20 supplies the electrical signals to the transmission linear phased array 11 under control of the controller 70, each transducer element of the transmission linear phased array 11 generates ultrasonic waves. In this case, when the transmitter 20 controls the time when an electrical signal is applied to each transducer element so that an ultrasonic wave is steered in the direction of an elevation angle $\phi=\phi m$, and is focused to an azimuth angle of $\theta=0°$ and a radial distance r=R, a transmission beam plane having a fan shape of the elevation angle $\phi=\phi m$ as shown in FIG. 2, is formed. The width of the transmission beam plane in the azimuth direction is determined by the size of the transducer element constituting the transmission linear phased array 11. Since a dynamic focusing cannot be performed during transmission, the beam width of the transmission beam plane in the elevation direction is minimal at r=R, and gets larger as it gets farther from R. Thus, only limiting area in the transmission beam plane becomes an effective area for three-dimensional image formation. Using a multi-zone focusing technique or a line focusing technique frequently used in an existing two-dimensional image formation apparatus with respect to each elevation angle, an effective transmission beam plane can be formed in a wider area or all desired areas. In this case, the transmitter 20 is modified according to the used technique.

The ultrasonic echoes reflect when the transmitted ultrasonic signal travels the inside of the human body are converted into electrical signals by the transducer elements of the reception linear phased array 12. The receiver 30 performs pre-amplification, time gain compensation, and filtering with respect to the ultrasonic signals converted by each reception transducer elements. Analog-to-digital (A/D) converters (not shown) which is provided in the receiver 30 convert the ultrasonic signals in digital form.

The parallel beam former 40 receives the digital ultrasonic signals output from the receiver 30 and performs a parallel beam forming with respect to the received digital signals. In more detail, the parallel beam former 40 performs a dynamic focusing with respect to all the points on a plane expressed as $\phi=0°$ and $\theta=\theta n$ in FIG. 2. As a result, a reception beam plane is formed and shown in parallel with the X-axis in FIG. 2. The reception beam plane crosses in perpendicular to the transmission beam plane having an elevation angle $\phi=\phi m$. A final pattern of the ultrasonic beam considering transmission and reception becomes a product of a transmission beam pattern and a reception beam pattern. Therefore, one scan line which is defined as a crossing line of a transmission beam plane having an elevation angle $\phi=\phi m$ with a reception beam plane having an azimuth angle $\theta=\theta n$ is obtained. The parallel beam former 40 performs apodization during parallel beam forming in order to reduce a side-lobe level.

If a dynamic focusing is performed with respect to all azimuth directions necessary for forming a three-dimensional image, that is, all azimuth angles $\theta=\theta n$ where n=1, 2, . . . , N during reception beam forming, the parallel beam former 40 can obtain all the scan lines from the transmission beam plane defined as an elevation angle $\phi=\phi m$. The beam width on the scan line obtained as described above is defined as follows: 1) The width of the elevation direction is same as that of the beam width of the transmission beam width. 2) The beam width and the resolution of the azimuth direction are the same as those of the reception beam plane, that is, the beam pattern of the azimuth direction is a one-way beam pattern of only the reception linear phased array 12. Thus, the resolution of the azimuth direction of the FIG. 2 apparatus can be controlled by controlling the transmitter 20, in such a manner that the resolution of the FIG. 2 apparatus is more excellent than that of the existing two-dimensional image formation apparatus.

As described above, the linear phased arrays 11 and 12 constituting the cross array 10 are used for transmission and reception, respectively and a parallel beam forming is performed at the time of reception, in order to perform a scan for one plane of image with a one-time transmission. That is, the FIG. 2 apparatus can scan one plane of a three-dimensional image when an existing two-dimensional image formation apparatus obtains a one-scan line. Thus, by repeating the above-described transmission and reception procedure by M times, an ultrasonic wave is focused with respect to $\theta=0°$ and different elevation angles $\phi=\phi m$ where m=1, 2, . . . , M for each transmission. A parallel beam forming is performed for $\phi=0°$ and all azimuth angles $\theta=\theta n$ where n=1, 2, . . . , N during reception, to thereby accomplish a three-dimensional scan. That is, a three-dimensional scan can be performed in M-times transmission or within the time taken when the existing two-dimensional image is obtained.

The image signal processor 50 performs various signal processing procedures for obtaining an excellent quality of image with respect to the signal focused on all the scan lines acquired in the parallel beam former 40, and performs an image processing and a picture signal processing for generating all types of two-dimensional images and three-dimensional images to be displayed on the display 60 using the thus-formed three-dimensional image data. The controller 70 performs control of all the operations and processing procedures, generation of the transmission pulses and transmission beam forming, the receiver, the parallel beam former, repeat control of the transmission and reception beam forming, and control of the image and signal processing.

In the three-dimensional image formation apparatus shown in FIG. 2, the number of both or each of the transmission and reception arrays, complexity of the transmitter 20 and the receiver 30 therefor are similar to those of the existing two-dimensional image formation apparatus. However, the complexity of the parallel beam former 40 for parallel-focusing all the scan lines constituting one section simultaneously can be several tens times that of the beam former in the existing two-dimensional image formation apparatus in view of size of the circuit and cost thereof. Thus, the present invention provides a more economic and realistic three-dimensional image formation apparatus using an three-dimensional image formation method which uses a cross array of the present invention in the structure of a general two-dimensional image formation apparatus as shown in FIG. 3.

The three-dimensional image formation apparatus of FIG. 3 adds a cross array, a data storage portion 180 and a three-dimensional image signal processor 190 in the existing two-dimensional image formation apparatus. The data storage portion 180 can be constituted by a number of semiconductor chips or a high-speed, large capacity hard disk. The three-dimensional image signal processor 190 can be constituted by a high-speed digital signal processor (DSP) or a large capacity, high-speed ASIC for specific calculation or routines. In FIG. 3, a transmitter 120, a receiver 130, a reception beam former 140 and a two-dimensional image signal processor 150 are the same as those of a general two-dimensional image apparatus. A transmission linear phased array 111 and a reception linear phased array 112 each of which comprised of 64 or 128 transducer elements are connected to the transmitter 120 and the receiver 130, respectively.

The output of the receiver 130 is input to the reception beam former 140 and the data storage portion 180, simultaneously. When the FIG. 3 apparatus operates at a normal mode, that is, a two-dimensional image mode, the transmission linear phased array 111 is used for performing a beam forming for only a fixed elevation angle $\phi=0°$, and the reception linear phased array 112 is used for performing a focusing of the received signal for only a fixed elevation angle $\phi=0°$ in each transmission. That is, one scan line only is obtained for each transmission and reception as in the existing two-dimensional image formation apparatus. In order to obtain a two-dimensional image, the transmitter 120 enables the transmission linear phased array 111 to operate so that a transmission beam plane is formed at an elevation angle of 0° in each transmission. The ultrasonic echo signals received in the reception linear phased array 112 are processed in the receiver 130, and then focused on a single scan line corresponding to one azimuth angle by the reception beam former 140. The focused signal is processed by the two-dimensional image signal processor 150 and displayed on the display 160. By repeating the above procedures, one plane of three-dimensional image can be formed, which is same as the existing two-dimensional image formation procedure. In the two-dimensional image mode, general linear phased arrays used in the existing two-dimensional image formation apparatus can be used.

The three-dimensional image mode using the FIG. 3 apparatus is performed in the following sequence: 1) A three-dimensional area to be scanned is determined using the two-dimensional image mode as described above. 2) A cross array 100 is positioned in the center of the determined three-dimensional area. 3) A transmission and reception procedure for three-dimensional scan described with reference to the FIG. 2 apparatus is performed, by depressing a specific button (not shown) for setting a three-dimensional image mode after completing the step 2). 4) The outputs of the receiver 130 corresponding to all the transducer elements of the reception linear phased array in each transmission in step 3) are stored in the data storage portion 180. 5) After completion of the above steps, that is, after all the transmission beam planes constituting a desired three-dimensional area are formed, and all the signals reflected from the planes and received in the transducer elements of the reception linear phased array are stored, the transmission and reception procedure stops.

The three-dimensional image signal processor 190 reads the data stored in the data storage portion 180, performs a beam focusing with respect to all scan lines in the three-dimensional scan area, and performs a required three-dimensional image processing, to thereby supply two-dimensional or three-dimensional image information to be displayed to the display 160.

The three-dimensional image formation method using the FIG. 3 apparatus as described above performs a scan operation (for transmission and reception) of a three-dimensional image formation on a real time basis, and performs reception beam focusing, three-dimensional image processing and restoring on a non-real time basis, while the FIG. 2 apparatus obtains the three-dimensional image on a real time basis. Although all the three-dimensional image formation procedures can be done as in the FIG. 2 apparatus on a real time basis, the three-dimensional image searching for obtaining clinical information can be done on a non-real time basis. Accordingly, the above-described method with reference to the FIG. 3 apparatus is also valid. Thus, a huge parallel beam former is not necessary as in the FIG. 2 apparatus.

The three-dimensional image signal processor 190 can be replaced by an externally linked computer. Here, the data storage portion 180 has a high-speed external computer interface. When such an external computer is used, the data storage portion 180 can be positioned in the external computer not in the three-dimensional image formation apparatus of FIG. 3. In any cases, the FIG. 3 three-dimensional image formation apparatus can be simply constructed in comparison with the FIG. 2 image formation apparatus.

As described above, the ultrasonic three-dimensional image formation apparatus of FIG. 3 can perform a real time four-dimensional scan when a memory capacity of the data storage portion 180 is sufficient. That is, the three-dimensional image information according to time can be obtained on a real time basis and then the change of the three-dimensional image can be checked according to time by performing reception beam focusing and image processing on a non-real time basis.

While only certain embodiments of the invention have been specifically described herein, it will apparent that numerous modifications may be made thereto without departing from the spirit and scope of the invention.

What is claimed is:

1. A method for forming an ultrasonic three-dimensional image using ultrasonic echoes, the method comprising the steps of:
   (a) forming a cross array by aligning a first linear phased array and a second linear phased array to cross perpendicular to each other and sharing a center transducer element, each of said first and said second linear phased arrays having linearly aligned, a predetermined size of square transducer elements, respective square transducer elements having a predetermined inter-element spacing;
   (b) transmitting ultrasonic waves via the first linear phased array so that all transmission beam planes necessary for scanning a desired three-dimensional area are formed;
   (c) receiving, via the second linear phased array, ultrasonic echoes produced by which the ultrasonic waves transmitted in step (b) are reflected from the desired three-dimensional area;
   (d) performing a parallel beam forming with respect to the ultrasonic echoes received in step (c), in order to obtain an ultrasonic signal involving a three-dimensional image from scan lines formed by individually crossing all the received beam planes necessary for scanning the desired three-dimensional area with each transmission beam plane formed in step (a); and
   (e) obtaining three-dimensional image information by signal-processing the ultrasonic signal obtained in step (d).

2. The ultrasonic three-dimensional image formation method according to claim 1, wherein said predetermined inter-element spacing is an half of an ultrasonic wavelength to be used and a length of one side in each transducer element is slightly smaller than the inter-element spacing.

3. The ultrasonic three-dimensional image formation method according to claim 1, wherein said each transmission beam plane is formed along an elevation direction having an elevation from a first normal plane perpendicular to the reception plane of the second linear phased array and parallel with the lengthy direction of the reception plane, and said each reception beam plane is formed along an azimuth direction having an azimuth from a second normal plane perpendicular to the transmission plane of the first linear phased array and parallel with the lengthy direction of the transmission plane.

4. The ultrasonic three-dimensional image formation method according to claim 3, wherein ultrasonic transmission using the first linear phased array is performed with respect to a fixed azimuth direction and ultrasonic reception using the second linear phased array is performed with respect to a fixed elevation direction.

5. The ultrasonic three-dimensional image formation method according to claim 4, wherein the direction where ultrasonic transmission is performed by the first linear phased array has the same azimuth angle as the first normal plane and the direction where ultrasonic reception is performed by the second linear phased array has the same elevation angle as that of the second normal plane.

6. The ultrasonic three-dimensional image formation method according to claim 1 wherein said step (c) comprises the step of:
   (c1) performing pre-amplification, time gain compensation and filtering with respect to the ultrasonic echoes received by the transducer elements of the second linear phased array; and
   (c2) converting the outputs of step (c1) in digital signals.

7. The ultrasonic three-dimensional image formation method according to claim 6, further comprising the step of storing the digital signals, and wherein said parallel beam forming step is performed with respect to the stored digital signals for dynamic focusing.

8. The ultrasonic three-dimensional image formation method according to claim 1, wherein said step (d) obtains a single image plane constituting a three-dimensional image with respect to a single elevation direction in a desired three-dimensional area.

9. An apparatus for forming an ultrasonic three-dimensional image using ultrasonic echoes, the apparatus comprising:
   a cross array which is formed by aligning a first linear phased array and a second linear phased array to cross perpendicular to each other and sharing a center transducer element, each of said first and said second linear phased arrays having, linearly aligned, a predetermined size of square transducer elements, respective square transducer elements having a predetermined inter-element spacing;
   a transmitter for transmitting ultrasonic waves via the first linear phased array so that transmission beam planes necessary for scanning a desired three-dimensional area are formed along elevation directions;
   a receiver for receiving ultrasonic echoes via the second linear phased array in which the ultrasonic echoes are obtained from each transmission beam plane formed by the transmitter, and converting the received ultrasonic echoes into digital form to then output the converted result;
   a beam former for storing the digital ultrasonic signals output from the receiver, and performing a parallel beam forming with respect to the stored ultrasonic signals in order to generate an ultrasonic signal involving a three-dimensional image from scan lines which are formed by individually crossing of all the received beam planes necessary for scanning a desired three-dimensional area with the transmission beam planes; and an image signal processor for signal-processing the ultrasonic signal beam-formed in the beam former and generating three-dimensional image information.

10. The ultrasonic three-dimensional image formation apparatus according to claim 9, wherein said predetermined inter-element spacing is an half of an ultrasonic wavelength to be used and a length of one side in each transducer element is slightly smaller than the inter-element spacing.

11. The ultrasonic three-dimensional image formation apparatus according to claim 9, wherein said each transmission beam plane is formed along an elevation direction having an elevation from a first normal plane perpendicular to the reception plane of the second linear phased array and parallel with the lengthy direction of the reception plane, and said each reception beam plane is formed along an azimuth direction having an azimuth from a second normal plane perpendicular to the transmission plane of the first linear phased array and parallel with the lengthy direction of the transmission plane.

12. The ultrasonic three-dimensional image formation apparatus according to claim 11, wherein said transmitter performs ultrasonic transmission using the first linear phased array with respect to a fixed azimuth direction and said receiver performs ultrasonic reception using the second linear phased array with respect to a fixed elevation direction.

13. The ultrasonic three-dimensional image formation apparatus according to claim 12, wherein the direction where ultrasonic transmission is performed by the first linear phased array has the same azimuth angle as the first normal plane and the direction where ultrasonic reception is performed by the second linear phased array has the same elevation angle as that of the second normal plane.

14. The ultrasonic three-dimensional image formation apparatus according to claim 9, wherein said receiver performs pre-amplification, time gain compensation and filtering with respect to the ultrasonic echoes received by the transducer elements of the second linear phased array, and then converts the results in digital signals.

15. The ultrasonic three-dimensional image formation apparatus according to claim 14, wherein said beam former performs a parallel beam forming with respect to the ultrasonic signals stored therein, and obtains an ultrasonic signal corresponding to a single image plane constituting a three-dimensional image with respect to a single elevation direction in a desired three-dimensional area.

16. The ultrasonic three-dimensional image formation apparatus according to claim 15, wherein said beam former comprises a storage medium for receiving and storing the digital ultrasonic signal output from the receiver on a real time basis.

17. The ultrasonic three-dimensional image formation apparatus according to claim 9, wherein said beam former and said image signal processor perform the signal processing on a real time basis.

18. The ultrasonic three-dimensional image formation apparatus according to claim 9, wherein said beam former comprises:

a single channel beam former for performing a beam forming for an existing ultrasonic two-dimensional image formation; and a storage medium having a capacity for storing an ultrasonic signal involving a three-dimensional image of one frame, and wherein said image signal processor comprises:

a two-dimensional image processor for signal-processing the ultrasonic signal output from the said single channel beam former and generating the two-dimensional image information; and a three-dimensional image processor for signal-processing the ultrasonic signal stored in said storage medium and generating three-dimensional image information.

19. The ultrasonic three-dimensional image formation apparatus according to claim 18, wherein said two-dimensional image processing is used in order to obtain an ultrasonic image information for determination of a desired three-dimensional area, and if the desired three-dimensional area is determined, the three-dimensional image information is obtained using said storage medium and said three-dimensional image processor.

20. The ultrasonic three-dimensional image formation apparatus according to claim 19, wherein the three-dimensional image information is acquired using said storage medium and said three-dimensional image processor on a real time basis.

21. The ultrasonic three-dimensional image formation apparatus according to claim 20, wherein said storage medium and said three-dimensional image processor can be embodied by a personal computer.

22. The ultrasonic three-dimensional image formation apparatus according to claim 9, wherein said beam former stores the ultrasonic signal for a certain time and performs a four-dimensional image processing by providing the change of the three-dimensional image according to time using the stored ultrasonic signal.

* * * * *